United States Patent
Bricot

(10) Patent No.: US 6,773,391 B1
(45) Date of Patent: Aug. 10, 2004

(54) DEVICE AND METHOD OF BIOSTIMULATING LIVING ORGANISMS AND/OR NEUTRALIZING THE HARMFUL EFFECTS OF APPLIANCES OPERATING WITH ELECTRIC POWER

(76) Inventor: Bernard Bricot, 367, Avenue du Prado, 33008 Marseille (FR)

( * ) Notice: Subject to any disclaimer, the term of this patent is extended or adjusted under 35 U.S.C. 154(b) by 0 days.

(21) Appl. No.: 10/088,105

(22) PCT Filed: Sep. 21, 2000

(86) PCT No.: PCT/FR00/02621

§ 371 (c)(1), (2), (4) Date: Jun. 12, 2002

(87) PCT Pub. No.: WO01/21252

PCT Pub. Date: Mar. 29, 2001

(30) Foreign Application Priority Data

Sep. 24, 1999 (FR) .......................... 99 12186

(51) Int. Cl.[7] .............. A61N 1/00; G09F 3/02
(52) U.S. Cl. .................. 600/15; 40/27.5
(58) Field of Search .......... 600/9, 15; 428/41.8, 428/900, 692, 318.6, 319.3, 420, 423.3; 136/225, 228; 602/138; 424/402, 489; 606/204, 189, 16; 128/898, 897, DIG. 3, 881; 601/23; 623/3.1; 12/147 R; 36/40, 44, 140, 141, 11.5; 54/83.1

(56) References Cited

U.S. PATENT DOCUMENTS

| | | | | |
|---|---|---|---|---|
| 1,665 A | * | 7/1840 | Warner et al. ............ 12/147 R |
| 658,027 A | * | 9/1900 | Steiger ..................... 600/15 |
| 4,033,054 A | * | 7/1977 | Fukuoka ................... 36/11.5 |
| 4,162,672 A | * | 7/1979 | Yazaki ..................... 600/15 |
| 4,391,270 A | * | 7/1983 | Uragami .................... 600/15 |
| 4,616,654 A | | 10/1986 | Bacchelli |
| 4,621,617 A | * | 11/1986 | Sharma ..................... 600/16 |
| 4,808,469 A | * | 2/1989 | Hiles ...................... 428/318.6 |
| 4,841,647 A | * | 6/1989 | Turucz ..................... 36/44 |
| 5,158,526 A | | 10/1992 | Bricot |
| 5,233,768 A | * | 8/1993 | Humphreys ................. 36/44 |
| 5,312,321 A | | 5/1994 | Holcomb |
| 5,642,739 A | * | 7/1997 | Fareed ..................... 128/881 |
| 5,782,743 A | * | 7/1998 | Russell .................... 600/9 |
| 5,792,176 A | * | 8/1998 | Chang ...................... 606/204 |
| 5,813,971 A | * | 9/1998 | Broderick .................. 600/15 |
| 5,965,282 A | * | 10/1999 | Baermann ................... 428/692 |
| 5,993,375 A | * | 11/1999 | Engel ...................... 600/15 |
| 6,148,822 A | * | 11/2000 | Cron et al. ................ 128/897 |
| 6,171,606 B1 | * | 1/2001 | Lyons ...................... 424/402 |
| 6,267,719 B1 | * | 7/2001 | Grisoni et al. ............. 600/15 |
| 6,277,142 B1 | * | 8/2001 | Pinter ..................... 607/1 |
| 6,322,491 B1 | * | 11/2001 | Bove et al. ................ 600/15 |
| 6,461,375 B1 | * | 10/2002 | Baudry et al. .............. 607/1 |

FOREIGN PATENT DOCUMENTS

| | | |
|---|---|---|
| CH | 183323 | 3/1936 |
| EP | 144610 | 6/1985 |
| FR | 2255922 | 12/1973 |
| FR | 2505660 | 11/1982 |
| FR | 2642654 | 8/1990 |
| WO | 93/24175 | 12/1993 |

* cited by examiner

Primary Examiner—Mary Beth Javes
Assistant Examiner—Nikita R Veniaminov
(74) Attorney, Agent, or Firm—Greenblum & Bernstein, P.L.C.

(57) ABSTRACT

Method and device for biostimulating living organisms and/or for neutralizing harmful effects of appliances that use electric power. The device includes a flat small plate that has at least two metallic components. One of the at least two metallic components includes a peripheral portion. Another of the at least two metallic components includes a central portion that is nested in the peripheral portion. Each of the central and peripheral portions include a metal or metal alloy. The device is adapted to at least one of treat various parts of a living organism and neutralizing the harmful effects of appliances that operate with electric power.

8 Claims, 2 Drawing Sheets

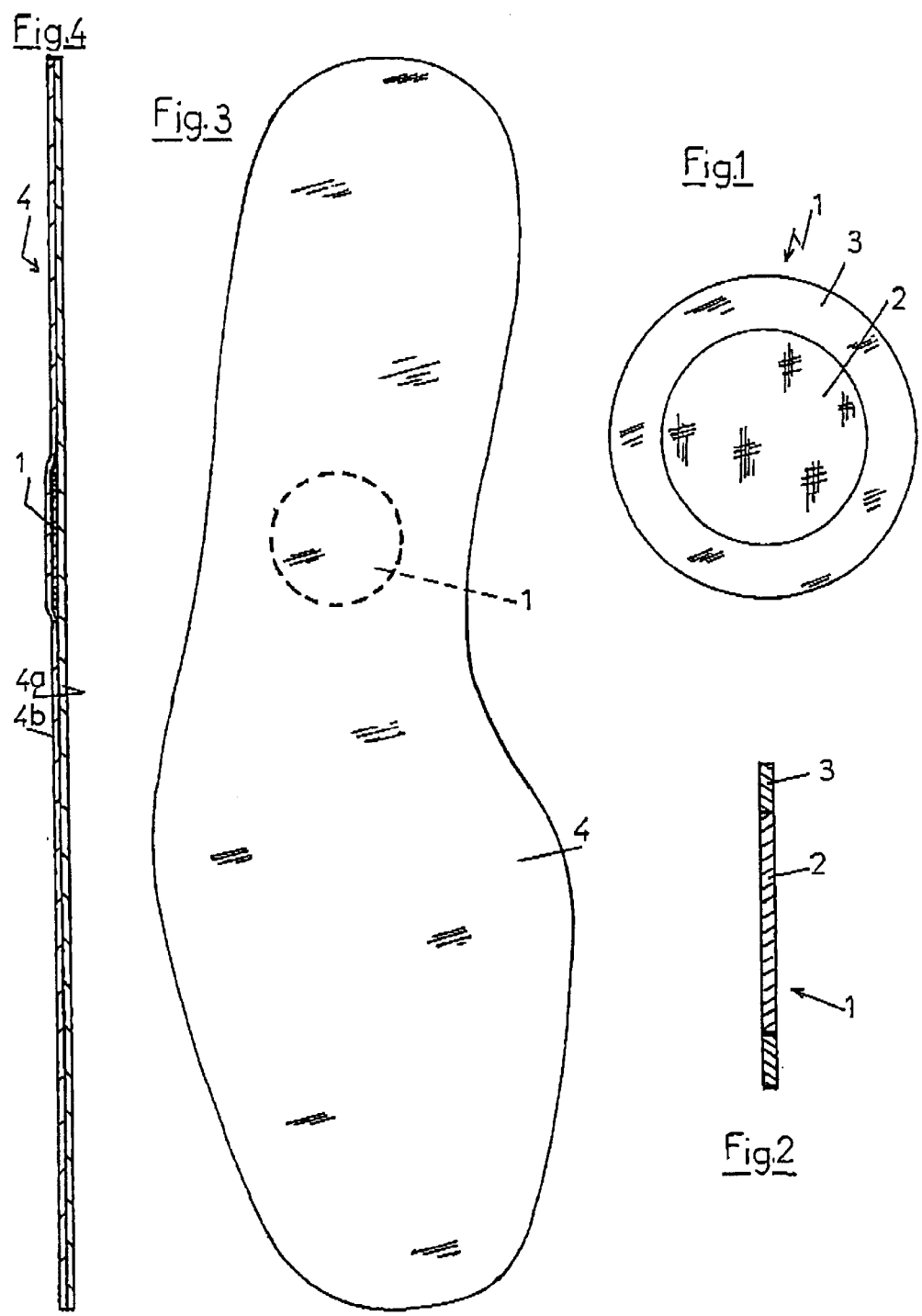

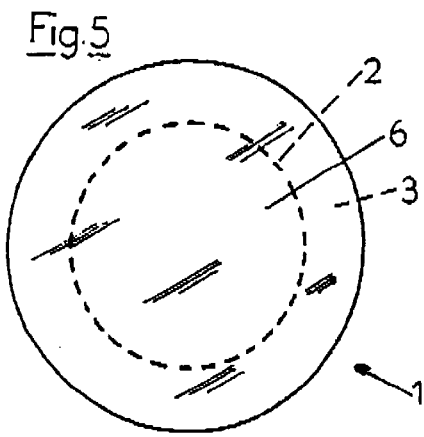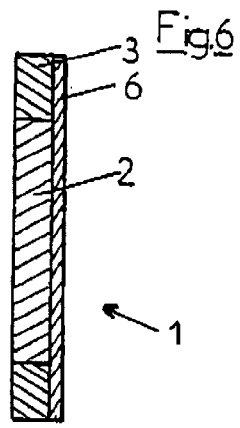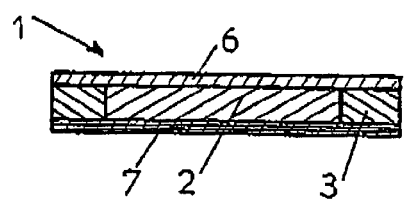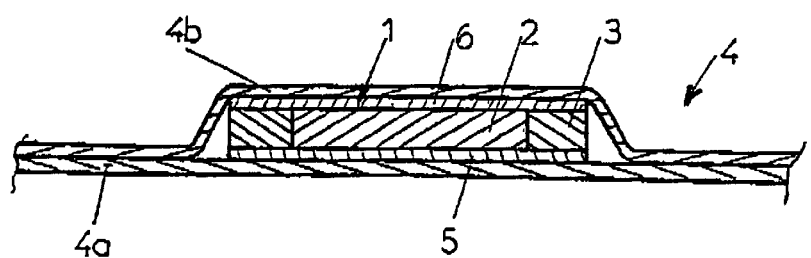

DEVICE AND METHOD OF BIOSTIMULATING LIVING ORGANISMS AND/OR NEUTRALIZING THE HARMFUL EFFECTS OF APPLIANCES OPERATING WITH ELECTRIC POWER

CROSS-REFERENCE TO RELATED APPLICATIONS

The present application is a National Stage Application of International Application No. PCT/FR00/02621, filed Sep. 21, 2000. Further, the present application claims priority under 35 U.S.C. §119 of French Patent Application No. 99/12186 filed on Sep. 24, 1999.

BACKGROUND OF THE INVENTION

1. Field of the Invention

The present invention relates to a device producing an electrogalvanic field or an electromagnetic field, and adapted to be positioned, according to a first application, in the vicinity of or in contact with certain parts or reflex zones of a living organism (person or animal) in view of their treatment or re-equilibration by stimulation or information; reference is then made to biostimulation. According to a second application, this device is adapted to be positioned on electrical appliances or in the vicinity thereof, in order to neutralize the harmful effects of the latter on the organism; reference is then made to neutralization or "bioneutralization."

2. Discussion of Background Information

It is known that a "postural invariant" exists, which represents the ideal position of the body in space, at a given moment in the phylogenic evolution of an individual. It has thus been possible to define criteria of normality in clinical posturology, which have led to the finding that more than 90% of individuals have a postural disequilibrium.

The disorders and diseases caused by the postural disturbances are extremely numerous. For example, spinal disorders or ailments (cervicalgia, lumbalgia, dorsalgia, etc.) can cause rachialgia, disorders related to standing (scoliosis, kyphosis, pelvic tilting, etc.), cephalgia (occipital headaches, cluster headaches, tension headaches), brachial plexus neuralgia, scapulalgia, and myalgia, low back pains, sciatica, and other disturbances influenced by rachidian disorders due to the close relationship between the spine and the autonomic nervous system, which is connected to all of the organs.

A large number of "functional" pathologies are thus caused, or at least markedly influenced by the postural disorders.

It is well established nowadays that it is preferable to treat postural disorders at their source, and not their symptoms only. It is known that the skin is capable of transmitting certain information that it receives to the brain (lemniscal and extralemniscal pathways), and that the brain is capable of analyzing such information. It is also known that it is possible to treat disorders or ailments caused by rachidian disequilibrium, by correcting certain cutaneous reflex zones or certain acupuncture points by means of micro-currents (diascope, punctoscope, etc.), laser radiations or magnetic fields; however, there are few devices that are adapted to correct these zones permanently. In particular, the document FR-2 255 922A describes galvanotherapy or acupuncture treating devices including two electrodes and one electrolyte in which a part of the patient's body is immersed. These devices are very cumbersome, due to the fact that they require a tank for immersing the patient's body part to be treated, and their complex handling requires the expertise of a skilled technician. Therefore, the effect of these currents remains sporadic, the duration of the electro-stimulation sessions and the desired results are uncertain, particularly due to the possible variations in distance between the body part to be treated and the stimulation electrode during the treatment session.

To overcome these drawbacks, the document FR-2 505 660A (and U.S. Pat. No. 5,158,526) has proposed postural reprogramming soles which, by polarizing the terrestrial radiation fields, apply a polarized undulatory flux of energy on the reflex zones of the feet, when they are in direct contact with the skin of the arch.

These postural reprogramming soles with polarizing fields yield good results, but it was desirous to have a device having a more complete and faster action, and which does not require to be placed in contact with the skin.

SUMMARY OF THE INVENTION

The present invention aims to remedy the disadvantages of the various known appliances and devices for treating the cutaneous reflex zones or other cutaneous zones, by utilizing electric fields or magnetic fields, by proposing a device that is easy to implement, efficient, even at a distance, and compact.

The electrogalvanic or electromagnetic field device according to the invention is made of the combination of at least two metallic components 2 and 3 constituted by various metals or by various metal alloys. This device is characterized in that it is made in the form of a flat, small plate 1 constituted by a central portion 2 nested in a peripheral portion 3. The central portion 2 and peripheral portion 3 are made of various metals or metal alloys. This device is used in a manner for treating various parts of a living organism, or a manner for neutralizing the harmful effects of appliances operating with electric power. This device is further remarkable for its use as a system for biostimulating various parts of a living organism, or for its use as a system for neutralizing the harmful effects of appliances operating with electric power.

In the first case, the biostimulating device is positioned in the vicinity of the reflex zone or of the part of the living organism to be treated, preferably by using various retention mechanism, or applied to the reflex zone. In the second case, the neutralizing device is fixed to the appliance operating with electric power.

Due to the different electrochemical character of the two metals constituting the electrogalvanic or electromagnetic field device according to the invention, an electrogalvanic field or electromagnetic field is generated, which re-equilibrates, stimulates, or informs the reflex zones, or interacts with the latter, next to which it is positioned, and/or neutralizes the disturbing micro-currents such as, for example, oral electrogalvanism, the disturbing fields of the portable phones on which it is positioned.

Due to its small size, the device according to the invention can be included in various retention mechanisms commonly used in clothing or in healthcare such as shoes, belts, corsets, bandages, wound-dressings, etc., or in various substances, such as resins, elastomers, plastic substances or the like, ionomeric glass, composite, etc. It can also be placed on the back of a watch, or directly on a portable phone or its battery.

According to a particularly advantageous embodiment, the invention can be constituted by a sole that is capable of being removably housed in a shoe, and between the superimposed constituent layers of which is inserted a small generator of electrogalvanic or electromagnetic fields, made in the form of a flat, small plate having a circular, square, rectangular contour or any other shape.

A major advantage of this device comes from the fact that it is not necessary to carry it in direct contact with the skin, so that it can be included and protected in a commonly used retention mechanism, without any notable transformation of the latter, while remaining fully efficient. For example, when it is placed at the level of each foot (or of only one foot, as the case may be), the symmetrical field (or asymmetrical field, as the case may be) thus generated makes it possible to equilibrate the postural muscular chains, which results in the following: a better equilibrium of the body; less muscular tensions; less vertebral blockages; a better posture and a better stability; and less vertebral and rheumatic pains, etc.

When it is made in the form of biostimulating soles enabling a re-equilibration of the postural muscular chains, the action of these soles is more complete and faster, compared to that of the soles with polarizing fields described in the document FR 2.505.660 A (and U.S. Pat. No. 5,158, 526). In particular, they work better and faster than the latter in all pathologies of vertebral or rheumatic pains or in pathologies with static or postural component (hips, knees, feet), and in all pathologies of spinal deformations (scoliosis) or limb deformations (misalignment, club feet).

The invention also provides for a device for biostimulating living organisms and/or for neutralizing harmful effects of appliances that use electric power, the device comprising a flat small plate that includes at least two metallic components, one of the at least two metallic components comprising a peripheral portion, another of the at least two metallic components comprising a central portion that is nested in the peripheral portion, and each of the central and peripheral portions comprising a metal or metal alloy, wherein the device is adapted to at least one of treat various parts of a living organism and neutralizing the harmful effects of appliances that operate with electric power.

The flat small plate may comprise a disc shape, wherein the peripheral portion comprises a washer and wherein the central portion comprises a circular pellet that is nested concentrically in the washer. Each of the central and peripheral portions may comprise various metals or metal alloys. The central portion may be made of copper and the peripheral portion may be made of zinc. The central portion may be made of zinc and the peripheral portion may be made of copper. Each of the central and peripheral portions may be arranged in the same plane.

The device may further comprise a mechanism which houses the device for biostimulating living organisms and/or for neutralizing harmful effects of appliances that use electric power. The mechanism may comprise a sole. The mechanism may comprise a retention mechanism. The retention mechanism may comprise one of a shoe, a belt, a corset, a bandage, and a wound-dressing. The device may be adapted to be applied against a part of a body of a living organism. The device may comprise a surface that is one of applied and adapted to be applied to a retention mechanism. The device may comprise a surface that is coated with a film of adhesive material. The device may comprise a surface adapted to be oriented toward a cutaneous zone to be stimulated, the surface being coated with a film of impervious material.

The device may further comprise a sole adapted to be applied beneath the sole of a foot of a user, the sole comprising two layers between which the device is installed.

The device may comprise a generator of fields or currents. The device may comprise a surface that is adapted to be applied to a retention mechanism, the surface being coated with a self-adhesive film.

The invention also provides for a method of treating parts of a living organism using the device, wherein the method comprises subjecting a part of the living organism to effects of fields or currents generated by the device.

The invention also provides a method of postural reprogramming a living organism using the device, wherein the method comprises subjecting a reflex zone of a foot or another cutaneous zone of a body to effects of fields or currents generated by the device.

The invention also provides for a method of neutralizing harmful effects of appliances operating with electric power using the device, wherein the method comprises subjecting an appliance to effects of fields or currents generated by the device.

The invention also provides for a device for biostimulating living organisms and/or for neutralizing harmful effects of appliances that use electric power, the device comprising a flat disc-shaped plate that includes at least two metallic components, one of the at least two metallic components comprising a washer having an opening, another of the at least two metallic components comprising a circular pellet that is nested in the opening of the washer, and each of the washer and the circular pellet comprising a metal or metal alloy, wherein the device is adapted to at least one of treat various parts of a living organism and neutralizing the harmful effects of appliances that operate with electric power.

The invention also provides for a device for biostimulating living organisms and/or for neutralizing harmful effects of appliances that use electric power, the device comprising a flat disc-shaped plate that includes at least two metallic components and two parallel surfaces, one of the at least two metallic components comprising a washer, another of the at least two metallic components comprising a circular pellet that is nested in the washer, each of the washer and the circular pellet comprising a metal or metal alloy, and at least one of the two parallel surfaces having an adhesive film disposed thereon, wherein the device is adapted to at least one of treat various parts of a living organism and neutralizing the harmful effects of appliances that operate with electric power.

BRIEF DESCRIPTION OF THE DRAWINGS

In the annexed drawings:

FIG. 1 is a front view of an interesting, although in no way limiting, example of embodiment, of the electrogalvanic or electromagnetic field device according to the invention;

FIG. 2 is a diametral cross-sectional view of the device shown in FIG. 1;

FIG. 3 is a front view of an example of retention mechanism incorporating the device according to the invention, this mechanism being constituted, according to this example, by a sole adapted to be housed in a shoe;

FIG. 4 is a longitudinal cross-sectional view of the sole shown in FIG. 3;

FIG. 5 is a front view of another example of an embodiment of the electrogalvanic or electromagnetic field device of the invention;

FIG. 6 is a diametral cross-sectional view of the device shown in FIG. 5;

FIG. 7 is a longitudinal cross-sectional view of a sole comprising a generator of electrogalvanic fields shown in FIGS. 5 and 6; and FIG. 8 is a diametral cross-sectional view of a third example of embodiment of the electrogalvanic or electromagnetic field device of the invention.

DETAILED DESCRIPTION OF THE INVENTION

Reference is made to said drawings to describe advantageous examples of non-limiting embodiments of the biostimulation or neutralization device according to the invention.

This device is remarkable in that it is made in the form of a flat, small plate 1 constituted of a central portion 2 nested in a peripheral portion 3. The central portion 2 and peripheral portion 3 are made of various metals or of various metal alloys. The biostimulating small plate can be made square, rectangular, circular, or have another shape.

According to the embodiment shown in FIG. 1, the generator of fields or currents of the invention is in the form of a small flat disc 1 constituted of a circular pellet 2 concentrically nested in a washer 3, this circular pellet and this washer being made of metals or metal alloys of various types and potentials.

Advantageously, these metals can be zinc and copper. Their combination makes it possible to constitute a battery or generator of electric current producing an electrogalvanic or electromagnetic field to re-equilibrate the cutaneous reflex zones, or to oppose the harmful effects of the disturbing electric micro-currents.

The central pellet 2 can be made of copper and the peripheral washer 3 of zinc, or vice versa.

However, it is not indispensable that the two metallic elements 2 and 3 be arranged concentrically; they could be attached in any other manner (end-to-end, side by side, etc.), such that the small plate 1 resulting from the combination of the elements could be square, rectangular, or have another shape.

On the other hand, the device according to the invention can be constituted of more than two metallic elements of different types (different metals or different metal alloys).

According to the invention, the small generator of electrogalvanic or electromagnetic currents is positioned in the vicinity of the reflex zones or of the parts of the body of the organisms to be treated, or applied to these reflex zones or parts. Let's specify that "in the vicinity" must be understood as designating any distances at which the reflex zones or other parts of the body can react to the effects of the currents or electrogalvanic or electromagnetic fields of the generator described in the present disclosure.

The electrogalvanic or electromagnetic field device according to the invention, can be included in a retention mechanism 4 that can be constituted by various commonly used articles, such as soles, shoes, belts, corsets, bandages, wound-dressings, or the like adapted to be applied against certain parts of the body of living organisms.

FIGS. 3 and 4 show an advantageous embodiment of the invention in the form of a biostimulation sole 4 constituted of two superimposed layers or thicknesses 4a, 4b, cut into one or several materials, such as leather, imitation leather, hide, imitation hide, cardboard, fabrics, felt, cork, plastic material, etc., between which is incorporated, according to any suitable method and at a location corresponding to the zone where the reflex zone(s) to be treated are found, a small generator 1 of electrogalvanic or electromagnetic fields made as indicated previously in the form of a flat, small plate, having a circular or other shape, whose components 2 and 3 are preferably arranged on a same plane.

Due to the fact that the pedal points of departure of the main ascending proprioceptive chains acting on the statural muscular groups are located in the zone of the plantar arch, and that the skin of the foot is particularly sensitive to the action of the electrogalvanic fields and to the frequential stimulation, the central zone of the sole of the foot is a particularly equilibrating part of the body, such that the small generator I of electrogalvanic fields can be positioned in the median zone of the sole 4.

The small generator 1 of electrogalvanic or electromagnetic fields can be glued to the lower surface 4a of the sole 4, by mechanism of a film 5 of adhesive material constituted, for example, of neoprene glue.

Preferably, a film 6 of impervious material covers the surface of the generator 1 adapted to be oriented toward the cutaneous zone to be stimulated, in order to prevent the corrosion of the generator, this film 6 being fixed to the surface, for example by way of neoprene glue.

It is understood that the sole according to the invention makes it possible to subject the reflex zones of the plantar arch to the biostimulating effects of the fields or currents generated by the small generator 1.

Of course, the generator of fields or currents can be housed in any other suitable area of the sole, depending on the reflex zone(s) that need to be stimulated.

The soles according to the invention can be removably housed in the users' shoes or can directly constitute the permanent soles for the treatment shoes.

In the first case, the surface of the generator 1, adapted to be removably fixed to a surface receiving the boot or any other retention mechanism, can be coated with a self-adhesive film 7 fixed to the surface, for example by way of neoprene glue (FIG. 7).

For guidance only, this flat, small disk 1 can have a diameter on the order of 10–50 mm and a thickness on the order of 1 mm.

It is noted that the charging and discharging frequency of the generator depends upon and thickness of the metals or metal alloys.

Is it easily understood that the electric fields emitted by the device according to the invention can be used to inform certain cutaneous zones whose ability to transmit the information to the high level center (lemniscal and extralemniscal pathways) are known, such that these electric fields can interact with the flux of potentials present in the human body, which can be stimulated in the case of a failure, or conversely can inform to neutralize the harmful effect of certain currents (oral electrogalvanism, disturbing fields of portable phones, etc.

It is understood that the invention relates to the method of postural reprogramming which consists of subjecting the reflex zones of the feet or other cutaneous zones of the body to the effects of the fields or currents generated by the previously described small generator of electrogalvanic fields.

The invention also relates to the use of the previously described electrogalvanic or electromagnetic field device to obtain a system for treating various parts of a living organism, and/or to obtain a system for neutralizing the harmful effects of appliances operating with electric power.

The invention also relates to a method of biostimulating living organisms, which includes subjecting the parts of the living organisms to be treated to the effects of the fields or currents generated by the device. Additionally, the invention relates to a method of neutralizing the harmful effects of appliances operating with electric power, which includes subjecting the appliances to the effects of the fields or currents generated by the device.

What is claimed is:

1. The mechanism comprises a sole.

2. The device according to of claim 1, wherein the device comprises a surface that is coated with a film of adhesive material.

3. The device according to claim 1, wherein the device comprises a surface adapted to be oriented toward a cutaneous zone to be stimulated, the surface being coated with a film of impervious material.

4. The device according to claim 1, further comprising a sole adapted to be applied beneath the sole of a foot of a user, the sole comprising two layers between which the device is installed.

5. The device according to claim 1, wherein the device comprises a surface that is adapted to be applied to a retention mechanism, the surface being coated with a self-adhesive film.

6. A device for at least one of, biostimulating living organisms and neutralizing harmful effects of appliances that use electric power, the device comprising:

a flat disc-shaped plate that includes at least two metallic components and two parallel surfaces;

one of the at least two metallic components comprising a washer which is a one-piece member;

another of the at least two metallic components comprising a circular pellet that is nested in the washer;

each of the washer and the circular pellet comprising one of a metal or metal alloy;

each of the washer and the circular pellet having the same overall thickness, whereby opposite parallel surfaces of the washer and opposite parallel surfaces of the circular pellet are arranged on the same planes; and at least one of the two parallel surfaces having an adhesive film disposed thereon, wherein said device is used to at least one of treat various parts of a living organism and neutralizing the harmful effects of appliances that operate with electric power.

7. The device according to claim 6, wherein each of the washer and the circular pellet is non-magnetic.

8. The device according to claim 7, wherein one of:

the washer comprises zinc and circular pellet comprises copper; and the washer comprises copper and the circular pellet comprises zinc.

\* \* \* \* \*

UNITED STATES PATENT AND TRADEMARK OFFICE
CERTIFICATE OF CORRECTION

PATENT NO. : 6,773,391 B1
DATED : August 10, 2004
INVENTOR(S) : B. Bricot

It is certified that error appears in the above-identified patent and that said Letters Patent is hereby corrected as shown below:

Title page,
Item [56], References Cited, U.S. PATENT DOCUMENTS, should read:
-- 6,189,197    02/2001        Kim, Won Hone        29/522.1 and

| | | | |
|---|---|---|---|
| —6,114,048 | 09-2000 | Jech et al. | 428/547— |
| —5,609,234 | 03-1997 | Walker et al. | 194/317— |
| —6,112,876 | 09-2000 | Juds et al. | 194/344— |
| —3,607,147 | 09-1971 | Harrison, Brian G. | 428/579— |
| —5,996,262 | 12-1999 | Kim, Won Hone | 40/27.5— |

Column 7,
Line 5, delete claim 1 in its entirety and insert the following:

— A device for biostimulating living organisms and/or for neutralizing harmful effects of appliances that use electric power, the device comprising
    a flat small plate that includes at least two metallic components;
    one of the at least two metallic components comprising a peripheral portion which is a one-piece member;
    another of the at least two metallic components comprising a central portion that is nested in the peripheral portion, the peripheral portion being arranged to completely surround a peripheral edge of the central portion;
    each of the central and peripheral portions comprising one of a metal or metal alloy;
    each of the central and peripheral portions having the same overall thickness, whereby opposite parallel external surfaces of the peripheral portion and opposite parallel external surfaces of the central portion are arranged on the same planes; and
    a mechanism which houses the device for at least one of, biostimulating living organisms and neutralizing harmful effects of appliances that use electric power,
    wherein the device is used to at least one of treat various parts of a living organism and neutralizing the harmful effects of appliances that operate with electric power, and
    wherein the mechanism comprises a sole.--

Lines 6-8, delete claim 2 in its entirety and insert the following:

— A device for biostimulating living organisms and/or for neutralizing harmful effects of appliances that use electric power, the device comprising:
    a flat small plate that includes at least two metallic components;
    one of the at least two metallic components comprising a peripheral portion which is a one-piece member;
    another of the at least two metallic components comprising a central portion that is nested in the peripheral portion, the peripheral portion being arranged to completely surround a peripheral edge of the central portion;
    each of the central and peripheral portions comprising one of a metal or metal alloy; and
    each of the central and peripheral portions having the same overall thickness, whereby opposite parallel external surfaces of the peripheral portion and opposite parallel external surfaces of the central portion are

UNITED STATES PATENT AND TRADEMARK OFFICE
CERTIFICATE OF CORRECTION

PATENT NO. : 6,773,391 B1
DATED : August 10, 2004
INVENTOR(S) : B. Bricot

It is certified that error appears in the above-identified patent and that said Letters Patent is hereby corrected as shown below:

Column 7 (cont'd),
Lines 9-12, delete claim 3 in its entirety and insert the following:

arranged on the same planes,
    wherein the device is used to at least one of treat various parts of a living organism and neutralizing the harmful effects of appliances that operate with electric power, and
    wherein the device comprises a surface that is coated with a film of adhesive material.—

Lines 9-12, delete claim 3, in its entirety and insert the following:

—- A device for biostimulating living organisms and/or for neutralizing harmful effects of appliances that use electric power, the device comprising:
        a flat small plate that includes at least two metallic components;
        one of the at least two metallic components comprising a peripheral portion which is a one-piece member;
        another of the at least two metallic components comprising a central portion that is nested in the peripheral portion, the peripheral portion being arranged to completely surround a peripheral edge of the central portion;
        each of the central and peripheral portions comprising one of a metal or metal alloy; and
        each of the central and peripheral portions having the same overall thickness, whereby opposite parallel external surfaces of the peripheral portion and opposite parallel external surfaces of the central portion are arranged on the same planes,
    wherein the device is used to at least one of treat various parts of a living organism and neutralizing the harmful effects of appliances that operate with electric power, and
    wherein the device comprises a surface adapted to be oriented toward a cutaneous zone to be stimulated, the surface being coated with a film of impervious material.—

Lines 13-16, delete claim 4 in its entirety and insert the following:

— A device for biostimulating living organisms and/or for neutralizing harmful effects of appliances that use electric power, the device comprising:
        a flat small plate that includes at least two metallic components;
        one of the at least two metallic components comprising a peripheral portion which is a one-piece member;
        another of the at least two metallic components comprising a central portion that is nested in the peripheral portion, the peripheral portion being arranged to completely surround a peripheral edge of the central portion;
        each of the central and peripheral portions comprising one of a metal or metal alloy;
        each of the central and peripheral portions having the same overall thickness, whereby opposite parallel external surfaces of the peripheral portion and opposite parallel external surfaces of the central portion are arranged on the same planes; and
        a sole adapted to be applied beneath the sole of a foot of a user, the sole comprising two layers between which the device is installed,
    wherein the device is used to at least one of treat various parts of a living organism and neutralizing the harmful effects of appliances that operate with electric power.—

UNITED STATES PATENT AND TRADEMARK OFFICE
CERTIFICATE OF CORRECTION

PATENT NO. : 6,773,391 B1
DATED : August 10, 2004
INVENTOR(S) : B. Bricot

It is certified that error appears in the above-identified patent and that said Letters Patent is hereby corrected as shown below:

Column 7 (cont'd),
Lines 17-20, delete claim 5 in its entirety and insert the folloiwng:

— A device for biostimulating living organisms and/or for neutralizing harmful effects of appliances that use electric power, the device comprising:
 a flat small plate that includes at least two metallic components;
 one of the at least two metallic components comprising a peripheral portion which is a one-piece member;
 another of the at least two metallic components comprising a central portion that is nested in the peripheral portion, the peripheral portion being arranged to completely surround a peripheral edge of the central portion;
 each of the central and peripheral portions comprising one of a metal or metal alloy; and
 each of the central and peripheral portions having the same overall thickness, whereby opposite parallel external surfaces of the peripheral portion and opposite parallel external surfaces of the central portion are arranged on the same planes,
 wherein the device is used to at least one of treat various parts of a living organism and neutralizing the harmful effects of appliances that operate with electric power, and
 wherein the device comprises a surface that is adapted to be applied to a retention mechanism, the surface being coated with a self-adhesive film. —

Signed and Sealed this

Twenty-eighth Day of December, 2004

JON W. DUDAS
*Director of the United States Patent and Trademark Office*